United States Patent

[19]

Basta

[11] Patent Number: 5,830,184
[45] Date of Patent: Nov. 3, 1998

[54] COMPOSITE CATHETER STABILIZING DEVICES, METHODS OF MAKING THE SAME AND CATHETER EXTRACTING DEVICE

[75] Inventor: Michael Ignazio Basta, Kulpsville, Pa.

[73] Assignee: Medical Components, Inc., Harleysville, Pa.

[21] Appl. No.: 611,927

[22] Filed: Mar. 6, 1996

Related U.S. Application Data

[63] Continuation of Ser. No. 611,927, Mar. 6, 1996.

[51] Int. Cl.$^6$ .................................................. A61M 29/00
[52] U.S. Cl. ............................ 604/104; 604/93; 604/174; 604/175; 604/280
[58] Field of Search .................................. 604/27–29, 43, 604/93, 96, 174, 175, 264, 265, 269, 280, 282, 104

[56] References Cited

U.S. PATENT DOCUMENTS

| | | | |
|---|---|---|---|
| 4,266,999 | 5/1981 | Baier ........................................ | 156/227 |
| 4,385,631 | 5/1983 | Uthmann . | |
| 4,405,313 | 9/1983 | Sisley et al. . | |
| 4,493,696 | 1/1985 | Uldall . | |
| 4,676,782 | 6/1987 | Yamamoto et al. ..................... | 604/175 |
| 4,863,426 | 9/1989 | Terragamo et al. ..................... | 604/93 |
| 5,053,023 | 10/1991 | Martin ..................................... | 604/28 |
| 5,084,013 | 1/1992 | Takase . | |
| 5,156,592 | 10/1992 | Martin et al. . | |
| 5,156,597 | 10/1992 | Verreet et al. . | |
| 5,171,216 | 12/1992 | Dasse et al. . | |
| 5,209,723 | 5/1993 | Twardowski et al. . | |
| 5,224,935 | 7/1993 | Hollands . | |
| 5,266,073 | 11/1993 | Wall . | |
| 5,308,338 | 5/1994 | Helfrich . | |
| 5,387,237 | 2/1995 | Fournier et al. ......................... | 623/11 |
| 5,487,730 | 1/1996 | Marcadis et al. ........................ | 604/96 |
| 5,509,902 | 4/1996 | Raulerson ................................ | 604/175 |
| 5,599,311 | 2/1997 | Raulerson ................................ | 604/175 |
| 5,638,813 | 6/1997 | Augustine .............................. | 128/207.15 |

OTHER PUBLICATIONS

B. Canaud, J.J.U. Beraud, H. Joyeux, C. Miou, "Internal Jugular Vein Cannulation with Two Silicone Rubber Catheters: A New and Safe Temporary Vascular Access for Hemodialysis", Artificial Organs 1986; 10(5):397–403.

F. Tesio et al., "Double Catheterization of the Internal Jugular Vein for Hemodialysis: Indications, Techniques, and Clinical Results", Artificial Organs 1994; 18(4): 301–304.

*Primary Examiner*—Wynn Wood Coggins
*Assistant Examiner*—Cris L. Rodriguez
*Attorney, Agent, or Firm*—Panitch Schwarze Jacobs & Nadel, P.C.

[57] ABSTRACT

A composite catheter stabilizing device, a catheter assembly including such a stabilizing device and a device for removing a catheter assembly are provided. The stabilizing device includes a cuff having a first and second edge which is configured to be positioned around a catheter. The device further includes a first and second end piece. The first and second end pieces have internal surfaces defining tubular openings which extend through the end pieces. The first and second end pieces are tapered from first sides which abut the edges of the cuff to second sides and the second sides of the end pieces are configured for receiving a catheter in facing engagement. The device for removing a catheter assembly includes a handle and a head having an external gripping surface which is sized for inserting into a lumen of a catheter assembly having a tissue ingrowth cuff for gripping an internal surface of the catheter assembly within the cuff and dislodging the cuff from surrounding tissue.

3 Claims, 3 Drawing Sheets

COMPOSITE CATHETER STABILIZING DEVICES, METHODS OF MAKING THE SAME AND CATHETER EXTRACTING DEVICE

CROSS-REFERENCE TO RELATED APPLICATION

This application is a continuation of application Ser. No. 08/611,927, filed Mar. 6, 1996, now abandoned, entitled Composite Catheter Stabilizing Devices, Methods of Making the Same and Catheter Extracting Device. The entire disclosure of application Ser. No. 08/611,927 as filed is incorporated herein by reference.

FIELD OF THE INVENTION

The present invention relates to a new catheter assembly, a catheter stabilizing device and a device for removing a catheter assembly having a catheter stabilizing device.

BACKGROUND OF THE INVENTION

Catheters, shunts, drainage tubes and the like, generally referred to herein as catheters, may be located in various locations within the human body for the introduction and removal of fluid from the body. Once in place, such catheters are typically anchored by a stabilizing device or sutured in place. Stabilizing devices generally are provided in several different types. Many catheters include a winged collar or cuff having suture holes formed in an outer area of the device. The collar or cuff freely rotates about the catheter. Catheters may also be taped to a patient's skin, however, taping alone is generally not sufficiently reliable to stabilize the device.

Another common catheter stabilizing device is a tissue-ingrowth cuff. Such a cuff is typically made of Dacron® or a similar biocompatible material, and is attached by an adhesive layer to the outer surface of a catheter cannula. The cuff is generally located on the catheter such that when a distal portion of the catheter is in position in a location to be catheterized, the cuff is positioned external to the catheterized part of the body, but below the surface of the skin in subcutaneous tissue.

In some cases, the cuff is positioned on the catheter such that when the distal portion of the catheter is inserted in the body part, the cuff is located in a subcutaneous tunnel. The tunnel is formed by a tunnelling tool, such as a trocar, either before or after cannulation of the vessel with the distal portion of the catheter. The proximal portion of the catheter having the cuff is drawn through the tunnel by the tool while the tool passes through the subcutaneous tissue. The cuff is generally sized such that when the procedure is done, the cuff will fit snugly in the tunnel or other area.

After a period of time, the surrounding tissue grows into the fabric of the cuff such that the catheter is stabilized in the catheterized location. In addition, the catheterized location and the subcutaneous tunnel are sealed off, preventing foreign bodies from entering the wound and blood from exiting or pooling around the catheter near the exit site, thereby preventing patient infection. While such fabric cuffs are inexpensive to make and are generally effective at stabilizing a catheter, they are also difficult to remove.

In order to remove such a cuff from ingrown subcutaneous tissue, such as a tunnel, a physician has to detach the cuff by cutting around the cuff with a scalpel. The physician has to cut the subcutaneous tissue surrounding all edges of the cuff into which tissue has grown. Tissue growth occurs substantially transverse to the longitudinal axis of the cuff around the outer circumference of the cuff. In addition, tissue growth occurs at angles oblique to the longitudinal axis of the cuff along both of the cuff's side edges. The physician must cut around the circumference of the cuff and both side edges to detach the cuff in a difficult, time-consuming surgical procedure that can increase patient bleeding. Such prolonged surgery and increased bleeding presents several risks to both the physician and patient, including the increased risk of infection. The procedure may also possibly contribute to an increased chance of scar tissue build-up within the subcutaneous area such that patients requiring multiple catheterization procedures may become increasingly difficult to catheterize.

The fabric cuffs also pose problems in the subcutaneous tunnelling procedures. Because the cuffs are sized to provide a snug fit in the subcutaneous area, they are difficult to pull smoothly through the tunnel. With catheters formed of softer durometer materials, such as pellethane and silicone, for example, the cuffs increase the risk that the catheter will snap or break apart during the tunnelling or removal procedure, and tend to elongate the tube and alter its dimensions. The stress placed on the proximal end of the catheter during the tunnelling procedure or during removal to pull the catheter through the tunnel is concentrated at the location of the cuff. As the cuff fits snugly within the subcutaneous tunnel, frictional forces against the tunnel wall affect the tunnelling and removal of the catheter. If the catheter breaks during removal, the physician may have to perform a further procedure to remove the broken-off distal portion of the catheter left within the patient. If the catheter breaks during the initial tunnelling procedure, the physician may have to completely recatheterize the patient.

Based on the foregoing disadvantages of prior art catheter stabilizing devices, particularly fabric cuffs, there is a need in the art for a stabilizing device which prevents the pooling of blood and invasion of foreign bodies by sealing a catheterized location, but which does not tend to break during placement or removal and which is easily removable without prolonged or invasive surgical cutting of subcutaneous tissue. There is also a need in the art for a device for safely removing such a stabilizing device from a subcutaneous location without the need for surgical cutting of the subcutaneous tissue.

SUMMARY OF THE INVENTION

The catheter stabilizing cuff of the present invention provides structural reinforcement to a catheter such that the catheter does not tend to break during catheterization or removal. It is easily removable without prolonged or invasive surgical cutting of subcutaneous tissue. Further, it can be removed without any surgical cutting when using the device for removing a catheter assembly of the present invention.

The present invention includes a composite catheter stabilizing device which includes a cuff and a first and second end piece. The cuff has a first edge and a second edge, and is configured for positioning around a catheter. The device also includes a first end piece and a second end piece. The first and second end pieces have internal surfaces which define tubular openings that extend through the end pieces. The first end and second end pieces have external surfaces which are tapered from their first sides to their second sides. The first sides of the first and second end pieces abut the first and second edges of the cuff, respectively. The second sides of the first and second end pieces are configured for receiving a catheter in facing engagement.

The invention also includes a catheter assembly which includes a catheter and a catheter stabilizing device. The catheter has an external surface and at least one lumen which extends through the catheter. The stabilizing device includes a cuff, a first end piece and a second piece. The cuff has a first edge and a second edge, and is adhered to the external surface of the catheter. The first and second end pieces have external surfaces and internal surfaces which are configured to conform to the external surface of the catheter in facing engagement. The external surfaces of the first and second end pieces are tapered from the first sides of the first and second end pieces, which respectively abut the first and second edges of the cuff, to the second sides of the first and second end pieces.

The invention also includes a method for making a catheter assembly having a composite catheter stabilizing device. A cuff having a first edge and a second edge is affixed to the external surface of a catheter. A first end piece having an internal surface, a first side and a second side is positioned around the external surface of the catheter such that the first side abuts the first edge of the cuff. A second end piece having an internal surface, a first side and a second side is positioned around the external surface of the catheter such that the first side abuts the second edge of the cuff. The first and second end pieces are tapered from their first sides to their second sides. The first and second end pieces are affixed to the external surface of the catheter such that the second sides of the end pieces are in facing engagement with the external surface of the catheter.

In an alternative embodiment, the method includes forming a unitary catheter which has an external surface, a lumen extending through the catheter, and a first and a second end piece. The first and second end pieces are tapered from the external surface of the catheter to first sides which lie in a plane perpendicular to the longitudinal axis of the catheter. The first sides of the first and second end pieces are facing and spaced from each other. A cuff having a first edge and a second edge is affixed to the external surface of the catheter between the first and second end pieces such that the first edge of the cuff abuts the first side of the first end piece and the second edge of the cuff abuts the first side of the second end piece. The end pieces and the cuff form the composite catheter stabilizing device.

An alternative embodiment of a composite catheter stabilizing device is included in the invention which includes a unitary base and a cuff. The base has an internal surface which defines a tubular opening that extends through the base and that has a first end piece, a second end piece, and an annular central portion positioned between the first and second end pieces. The first end piece has an external surface tapered from a first side toward a second side, the second end piece has an external surface tapered from a first side to a second side and the internal surface is configured for positioning around a catheter. The cuff has a first edge that abuts the first side of the first end piece and a second edge that abuts the first side of the second end piece. The cuff is configured for positioning around the central portion of the base.

An alternative method is also provided for making a catheter assembly having a composite catheter stabilizing device. The method includes affixing a base to the external surface of the catheter. The base has an internal surface which defines a tubular opening and has a first end piece, a second end piece and a central portion. The base is affixed to the catheter such that the internal surface of the base is in facing engagement with the external surface of the catheter. The external surfaces of the first and second end pieces are each tapered from a first side to a second side. A cuff is affixed to the external surface of the central portion of the base such that a first edge of the cuff abuts the first side of the first end piece and a second edge of the cuff abuts the first side of the second end piece.

A device for removing a catheter assembly having a catheter stabilizing device including a tissue ingrowth cuff from a subcutaneous location is also provided in the present invention. The device includes a handle and a head. The handle has a proximal end, and a distal end. The head is attached to the distal end of the handle, and has an external gripping surface. The head is sized for insertion into a lumen of a catheter assembly having a tissue ingrowth cuff for gripping an internal surface of the catheter assembly within the cuff and dislodging the cuff from surrounding tissue.

A method for removing a catheter assembly having a catheter stabilizing device including a tissue ingrowth cuff which is grown into a subcutaneous location is also included in the present invention. The catheter assembly is removed by a device having a handle and a head having an external gripping surface. The method includes inserting the head of the device into a proximal end of a lumen extending through the catheter assembly, inserting the head further into the lumen by pushing the handle of the device until a distal end of the head is substantially longitudinally aligned with a distal end of the tissue ingrowth cuff, and pulling the handle to dislodge the tissue ingrowth cuff and to remove the catheter assembly from the subcutaneous location.

BRIEF DESCRIPTION OF THE DRAWINGS

The following description of the preferred embodiment of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF PREFERRED EMBODIMENTS

Certain terminology is used in the following description for convenience only and is not limiting. The words "right," "left," "lower," "upper," "downward" and "outward" designate directions in the drawings to which reference is made. The terminology includes the words above specifically mentioned, derivatives thereof, and words of similar import.

Figure 1:
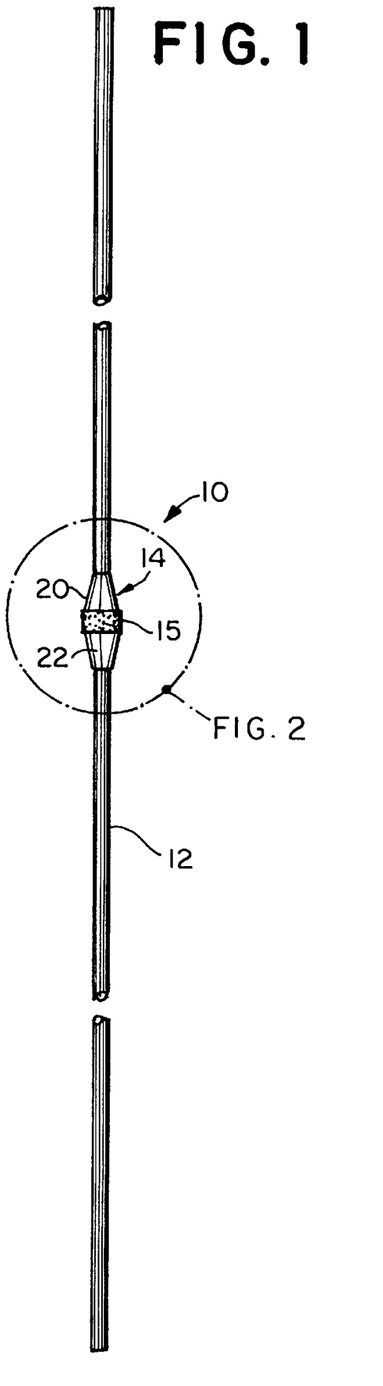
FIG. 1 is a plan view of a preferred embodiment of a catheter having a stabilizing device affixed to the external surface of the catheter according to the present invention.

Referring now to the drawings in detail, there is shown in FIG. 1 a catheter assembly, generally designated as 10, having a catheter 12 and a stabilizing device 14 according to the present invention. The catheter 12 has an external surface 16 and at least one lumen 18 extending therethrough. It will be understood, based on this disclosure, that the catheter 12 may be any catheter suitable for introducing or removing fluid from the body which requires subcutaneous securement, including, for example, a Tesio catheter, a single-lumen catheter, a shunt or drainage tube, a parenteral nutrition catheter, an oncologic catheter, a peritoneal dialysis catheter, a dual-lumen catheter, a triple-lumen catheter and the like.

The catheter 12, and the stabilizing device 14 may be formed of the same or different materials. Either or both of the catheter 12 and the stabilizing device 14 are preferably made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheter 12 and/or the stabilizing device 14, it is most preferred that the polymeric material includes a polyurethane or a polyolefin polymeric material.

Suitable, preferred, biocompatible elastomers for use in forming the catheter 12 and the stabilizing device 14 include biocompatible elastomers such as medical grade silicone rubbers, polyvinyl chloride elastomers, polyolefin homopolymeric and copolymeric elastomers, urethane-based elastomers, and natural rubber or other synthetic rubbers. The catheter may be formed of any of the above materials, or similar materials, depending upon the particular application of the catheter 12. For the purposes of describing the preferred embodiment of the assembly 10 herein, the stabilizing device 14 will be described in combination with a single-lumen Tesio catheter as shown in FIG. 1, however, it should be understood, that the invention is not limited to use on Tesio catheters.

Preferably, the stabilizing device 14 is made of elastomeric material such that the stabilizing device 14 is flexible, durable, and easily conformable to the shape of the subcutaneous location in which the catheter 12 is to be stabilized. The material used for making the device 14 may be of varying degrees of hardness. It is preferred that if the catheter 12 and the stabilizing device 14, are used for hemodialysis applications particularly, that they be formed of a silicone elastomer which preferably has a hardness of at least about 80-A on a Shore durometer scale. While it is preferred to have a higher Shore durometer hardness if a biocompatible elastomer is used, particularly for hemodialysis, it is also possible to make a device from an elastomer having a lower Shore durometer hardness without departing from the spirit of the invention.

It will be understood, based on this disclosure, that the catheters 12 and stabilizing device 14 may also be radiopaque depending on their intended use.

The device 14 includes a cuff 15, preferably including a material such as Dacron® polyester and similar materials which are useful for forming tissue ingrowth cuffs in a manner which will be known to those skilled in the art based on this disclosure. Such a cuff may further be impregnated with, for example, antibacterial substances, silver, antibiotics and the like. While a fabric tissue ingrowth cuff is preferred, the cuff 15 may also be formed of other biocompatible materials, or biocompatible materials having a fabric tissue ingrowth cuff on their external surface, as long as the device 14 includes a means for stabilizing the device 14 within a subcutaneous location.

The cuff is configured for positioning around a catheter, for example, if a fabric cuff 15 is used, the cuff 15 is cut into a generally rectangular-shaped piece of fabric and then fitted on a proximal portion of the catheter 12 which will be positioned in a subcutaneous location for stabilizing the catheter 12. The location of the cuff 15 and the device 14 on the catheter 12 depends upon the particular application of the catheter. For example, for a Tesio catheter, the device 14 would be positioned such that the cuff 15 would lie within a subcutaneous tunnel formed proximal to a vessel in the body, such as the internal jugular vein, when that vessel has been catheterized with a distal portion of the catheter 12. Surrounding tissue cells within the tunnel will grow into the fabric cuff 15 stabilizing the catheter in the subcutaneous location.

Figure 2:
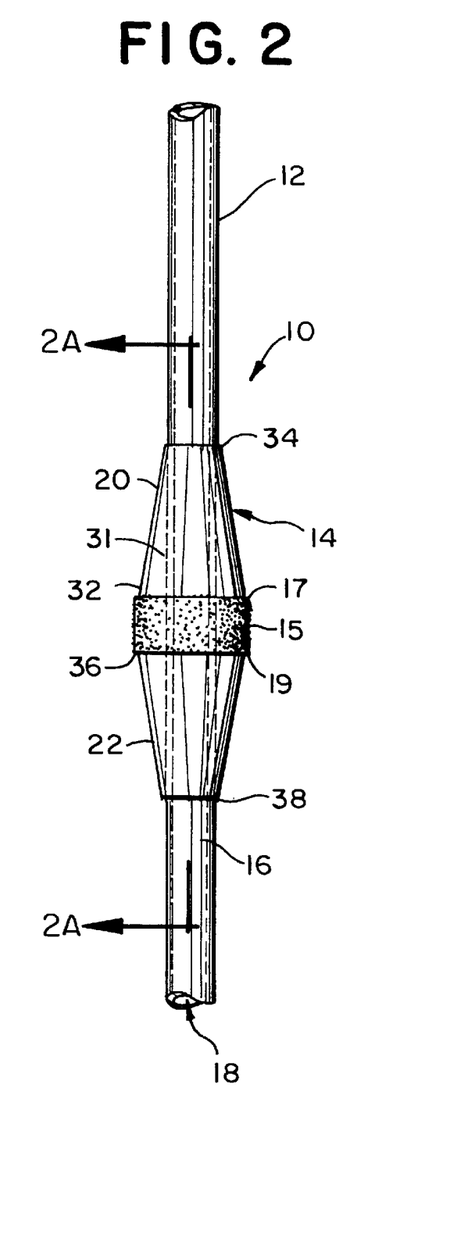
FIG. 2 is an enlarged plan view of the catheter stabilizing device of FIG. 1.
Figure 2A:
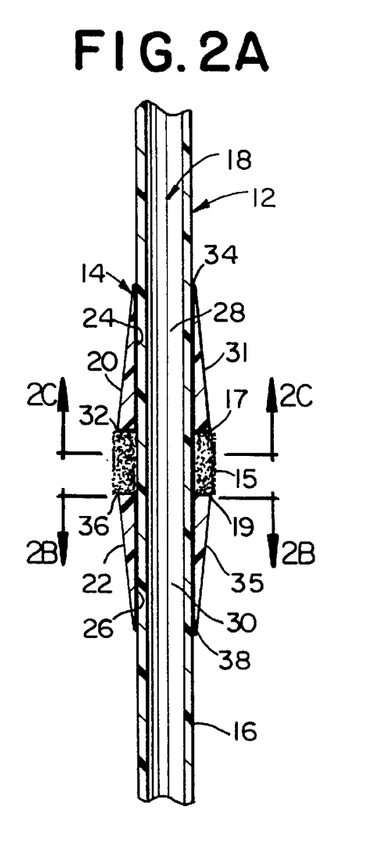
FIG. 2A is cross-sectional view of the catheter stabilizing device of FIG. 2 taken along line 2A—2A.

The generally rectangular portion of fabric is wrapped around the catheter preferably only one time without any overlapping of the fabric. The fabric cuff is affixed or adhered to the external surface 16 of the catheter 12 to form the cuff 15. The cuff may be affixed by any suitable medical grade adhesive. Any suitable pressure or heat sensitive medical grade adhesive may be used such as, for example, Dow Corning Silicone Medical Grade Adhesive. However, other biocompatible adhesives are also acceptable. Once the cuff 15 is positioned around the catheter 12, the cuff 15 has a first edge 17 and a second edge 19 as shown in FIGS. 2 and 2A.

The first end piece 20 and the second end piece 22 of the stabilizing device 14 preferably have respective internal surfaces 24, 26 which define respective tubular openings 28, 30 that extend through the end pieces and which are preferably configured to conform to the external surface of the catheter on which they are used, preferably in facing engagement. The openings 28, 30 are preferably generally cylindrically shaped for use on catheters having a generally circular cross section. However, the cross section of the openings 28, 30 may be oval, elliptical or other similar shapes depending primarily on the shape of the catheter on which the device is to be used.

The first end piece 20 has an external surface 31 which is tapered from a first side 32 which abuts the first edge 17 of the cuff 15 to a second side 34. The end piece 20 is tapered radially such that the outer diameter of the first side 32 is larger than the outer diameter of the second side 34. The decrease in the diameter from the first side 32 to the second side 34 may be constant over the end piece 20 such that a preferred frustoconically-shaped end piece 20 is formed or may be variable such that a more curved shaped end piece 20, for example, a "football"-shape, a "bullet"-shape or similar elliptical shape, is formed.

If the end piece 20 is tapered with a constantly decreasing diameter to form a frustoconically-shaped end piece, depending upon the diameter of the first side 32, the angle corresponding to the slope of the taper, as measured between the longitudinal axis of the catheter and the external surface of the end piece 20 may range from about 20° to 75°, preferably about 25° to about 50°, and more preferably about 40° to about 50°. The angle may be smaller or larger depending upon several factors, including, the material of construction of the catheter, the width of the opening 28, and the type of tissue in which the device will be located. For example, a device having a smaller width opening 28 such as 9 FR would be typically used with a catheter having a comparably small diameter. Smaller catheters in general, may require additional reinforcement and will be used in smaller subcutaneous locations such that the angle of taper will also be smaller. An end piece 20 as used on a larger diameter catheter, for example, an 18 FR catheter, may require a larger angle of taper.

When the catheter is formed of a material which is more likely to break upon application of a pulling force on the catheter, i.e., a silicone material, may require a smaller angle of taper than necessary with more resilient materials to provide additional structural reinforcement to the catheter.

The second end piece 22 also has an external surface 35 which is tapered from a first side 36 which abuts the second edge 19 of the cuff 15 to a second side 38 in the same manner as the first end piece 20. The second sides 34, 38 of the end pieces 20, 22 are preferably configured to receive the external surface 16 of the catheter 12 in facing engagement to prevent fluid from entering the device.

Figure 2B:
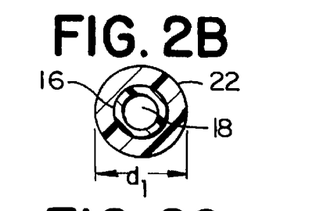
FIG. 2B is a cross-sectional view of the catheter stabilizing device of FIG. 2A taken along line 2B—2B.
Figure 2C:
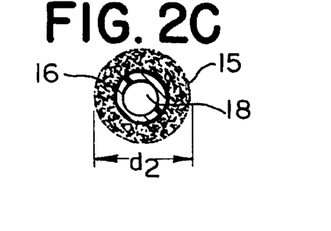
FIG. 2C is a cross-sectional view of the catheter stabilizing device of FIG. 2A taken along line 2C—2C.

In the preferred design shown in FIGS. 2A to 2C, the first sides 32, 36 of the first and second end pieces 20, 22 have generally annular cross-sections which lie in planes generally perpendicular to the longitudinal axis of the catheter 12. Preferably, the first sides 32, 36 have a cross-sectional diameter $d_1$ as shown in FIG. 2B which is substantially the same as the cross-sectional outer diameter $d_2$ of the cuff 15 as shown in FIG. 2C when it is positioned around the catheter 12 as shown in FIGS. 2A to 2C. The first sides 32, 36 when positioned against the cuff 15 should be flush with the edges 17, 19 of the cuff to substantially prevent tissue ingrowth into the edges 17, 19 of the cuff.

It is also preferred that the first and second end pieces 20, 22 are frustoconically shaped to facilitate passage through the subcutaneous location in which the catheter 12 is to be stabilized. The tapered portion and decreased diameter of the end pieces 20, 22 helps reduce friction and drag while moving through a subcutaneous location, but the diameter of the cuff is still capable of providing a sufficiently snug fit in the subcutaneous location to allow for prevention of bleeding and for promoting tissue ingrowth.

In addition, while it is possible to form the end pieces 20, 22 such that they are hollow and only in facing engagement with the external surface 16 of the catheter 12 at their second sides 34, 38, it is preferred, for stronger structural integrity, that the first and second end pieces 20, 22 are solid, as shown in FIG. 2, along their entire length. As such, it is preferred that the internal surfaces 24, 26 be flush with the internal surface 16 of the catheter 12. By forming the device 14 in this manner, the risk of blood or tissue entering between the device 14 and the catheter 12 is minimized.

Figures 3, 4:
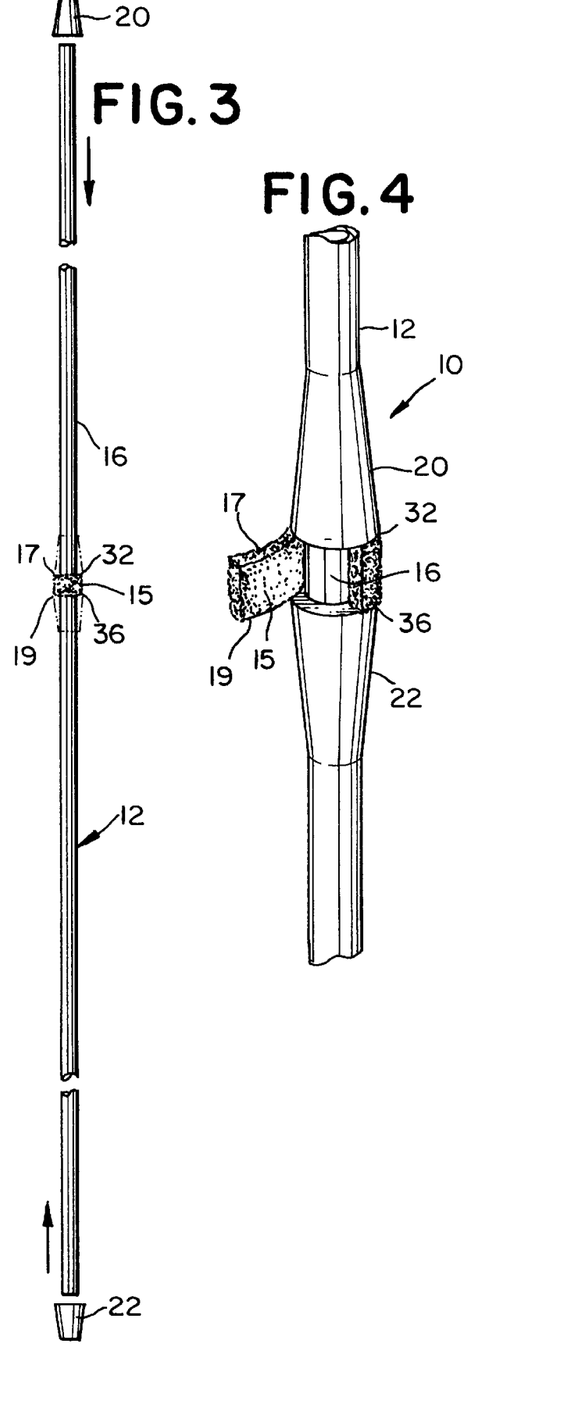
FIG. 3 is a plan view of a preferred method for making a catheter assembly having a composite catheter stabilizing device according to the present invention.
FIG. 4 is an enlarged perspective view of an alternative method for making a catheter assembly having a composite catheter stabilizing device according to the present invention.

The end pieces 20, 22 may be separately formed and heat-molded to the catheter 12 after manufacture of the catheter 12 by any suitable heat-molding method, including injection molding, transfer molding, RF induction and the like. Alternatively, they may be integrally formed by using such heat-molding methods to form the catheter 12 as a unitary catheter having the end pieces 20, 22 pre-formed on the external surface 16 as shown in FIG. 4. If the end pieces 20, 22 are separately formed, they may also be affixed to the external surface 16 of the catheter 12 by a medical grade adhesive, by ultrasonic welding using an ultrasonic horn in a manner which will be known to those skilled in the art or by any other suitable method of adhesion.

Figures 5, 5A, 6:
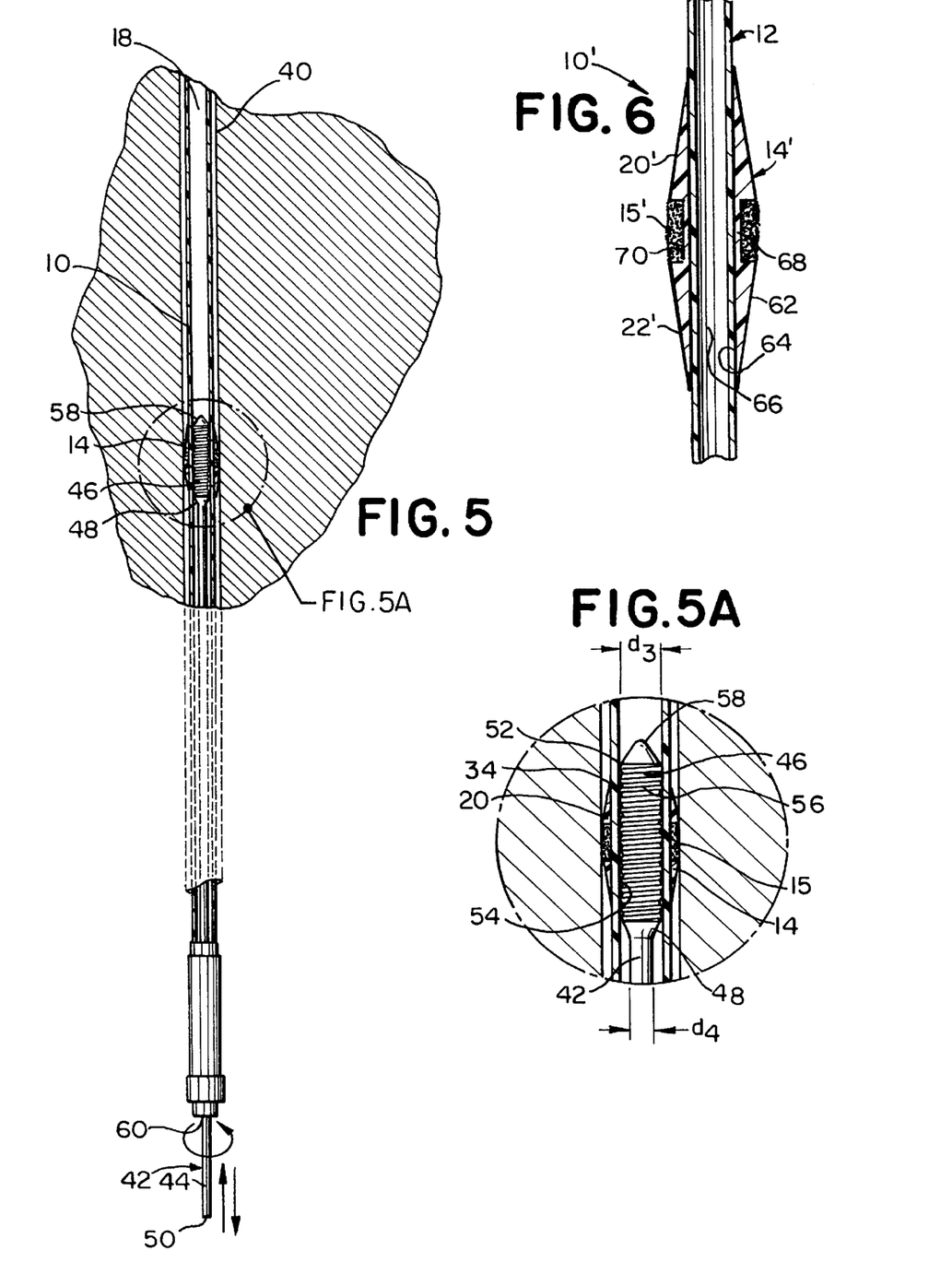
FIG. 5 is a partially broken away perspective view of a catheter assembly according to the present invention being removed from a subcutaneous location with a removal device according to the present invention.
FIG. 5A is an enlarged portion of the catheter assembly and removal device of FIG. 5 enclosed within the broken circle.
FIG. 6 is a cross-sectional view of a catheter having an alternative embodiment of a stabilizing device according to the present invention.

An alternative embodiment of a catheter assembly 10' is shown in FIG. 6. The alternative assembly 10' includes a catheter 12 and a composite catheter stabilizing device 14' which includes a unitary base 62. The catheter may be any suitable catheter 12 as described above with respect to assembly 10. The base 62 has an internal surface 64 which defines a tubular opening 66 that extends through the device 14'. The internal surface 64 is configured for positioning around a catheter 12. The base 62 may be formed of the same materials used to form the first and second end pieces 20, 22 of assembly 10.

The base 62 is integrally formed of a first end piece 20', a second end piece 22' and an annular central portion 68 positioned between the ends 20', 22'. The end pieces 20', 22' are identical to the end pieces 20, 22 described above, with the exception that they are interconnected by the central annular portion 68. The unitary base 62 may be separately formed, or formed as a part of a unitary catheter assembly in the manner shown in FIG. 4, and as described herein, with respect to the catheter assembly 10.

If formed independently of the catheter 12, the base 62 may be affixed to the external surface of the catheter 12 by any suitable heat molding method or by use of adhesive, ultrasonic welding or any other suitable method of adhesion. By connecting the end pieces 20', 22' with the central portion 68 to form a unitary base 62, the device 14' has enhanced structural integrity which may provide further reinforcement for the catheter 12 within the assembly when pulling the proximal portion of the catheter through a subcutaneous location.

A cuff 15' has a first edge abutting the first side of the first end piece 20' and a second edge abutting the first side of the second end piece 22' in a manner similar to that shown with respect to assembly 10. The cuff 15' is configured for positioning around the exterior surface 70 of the annular central portion 68 as shown in FIG. 6. The cuff may be affixed to the central portion 68 by any suitable method, for example, in the same manner as the cuff 15 is affixed to the external surface of the catheter 12 in the composite device 14 of assembly 10 described above.

Methods for making the catheter assembly 10 having a composite catheter stabilizing device are also included in the present invention. In one embodiment as shown in FIG. 3, a cuff, such as the cuff 15 described above, is affixed to the external surface 16 of a catheter, such as the catheter 12 described above. Preferably, a tissue ingrowth fabric cuff having an adhesive layer on one surface of the cuff 15 is wrapped around the external surface of the catheter 12 such that the adhesive affixes the cuff 15 to the catheter in the manner shown in FIG. 3.

A first end piece 20 having an internal surface 24 which defines a tubular opening 28 as shown in FIG. 2A is positioned around the external surface 16 of the catheter such that the first side 32 of the end piece 20 abuts the first edge 17 of the cuff 15. The second end piece 22 has an internal surface 26 which defines a tubular opening 30 as shown in FIG. 2A. The end piece 22 is positioned around the external surface 16 of the catheter 12 such that the first side 36 abuts the second edge 19 of the cuff 15.

The first and second end pieces 20, 22 are affixed to the external surface of the catheter such that the internal surfaces 24, 26 of the end pieces 20, 22 are preferably in facing engagement with the external surface 16 of the catheter 12. Preferably, the first and second end pieces are affixed to the catheter 12 by any suitable method of heat-molding the first and second end pieces onto the catheter in a manner which will be understood by those skilled in the art. Preferably, the first and second end pieces 20, 22 are affixed to the catheter by a suitable method of transfer molding. Alternatively, the first and second end pieces may be affixed to the external surface of the catheter 12 by use of an adhesive or by ultrasonically welding the pieces 20, 22 to the external surface 16.

In an alternative method for making a catheter assembly having a composite catheter stabilizing device, a unitary catheter 12 is formed by preferably heat molding a biocompatible polymer such as those described above. The mold should be shaped to form a unitary catheter 12 having a first end piece and a second end piece in a single unit as shown in FIG. 4. Any heat-moldable process may be used to form the unitary catheter 12. The end pieces may be formed in the same manner, and will be referred to for the purposes of describing the method, as similar to the first and second end pieces 20, 22 described above. The first end piece 20 is radially tapered from an external surface of the catheter 12 toward a first side 32, which preferably lies in a plane perpendicular to the longitudinal axis of the catheter 12 as shown in FIGS. 2 and 4. The second end piece 22 is radially tapered from the external surface of the catheter toward a first side 36 lying in a plane perpendicular to the longitudinal axis of the catheter. The first side of the first portion 20 and the first side of the second portion 22 of the unitary molded catheter should be facing each other, but spaced apart as shown in FIG. 4.

A cuff 15, such as that described above having a first edge 17 and a second edge 19 is affixed to the external surface 16 of the catheter 12 by a suitable adhesive between the first and second end pieces 20, 22 such that the first edge 17 of the cuff 15 abuts the first side 32 of the first end piece 20 and the second edge 19 of the cuff 15 abuts the first side 36 of the second end piece 22.

The method for making the composite assembly 10', shown in FIG. 6, may be described with reference to FIGS. 3, 4 and 6. A unitary base 62, as shown in FIG. 6 and described above, is affixed to the external surface of the catheter 12 such that the internal surface 64 of the base 62 is in facing engagement with the external surface of the catheter. The base 62 may be affixed to the catheter by sliding the base 62 along the catheter and affixing the base 62 to the external surface with an adhesive, by any suitable heat-molding method, or by ultrasonic welding, in a manner similar to the method as shown in FIG. 3 for the assembly 10.

Alternatively, the base as shown in FIG. 6 may be integrally molded with a catheter 12 to form a unitary assembly 10' in a manner similar to the method of forming the unitary assembly 10 including the device 14 as shown in FIG. 4.

The cuff 15' is then affixed to the external surface 70 of the annular central portion 68 of the base 62 by any suitable method of adhesion such that the edges of the cuff 15' abut the first sides of the first and second end pieces 20', 22'. The cuff 15' may be affixed to the central portion 68 by any suitable method such as those described above with respect to affixing the cuff 15 to the external surface of the catheter 12 when making assembly 10.

By forming a composite stabilizing device 14 or 14' such as those described above, the removal of the catheter 12 from the subcutaneous location is greatly simplified and improved. Because of the design of the device 14, 14' as shown in FIGS. 1, 2, 2A, 4 and 6, wherein the edges 17, 19 of the cuff abut the end pieces 20, 22, growth of subcutaneous tissue into the first and second edges 17, 19 of the cuff, as occurs with ordinary stabilizing cuffs, is substantially prevented and tissue grows only in a direction generally perpendicular to the longitudinal axis of the catheter assembly. The positioning of the end pieces 20, 22 substantially prevents tissue from growing into the edges 17, 19 of the cuff. Thus, to remove the catheter, the physician need only cut around the external circumference of the cuff to extricate the cuff from the subcutaneous tissue.

The tapered design of the end pieces allows for a smoother passage of the cuff through a subcutaneous area, while still providing a sufficiently snug fit for tissue ingrowth. Further, the stabilizing devices 14, 14' provide additional reinforcement to the catheter at the point where the most stress is applied in pulling the catheter through a subcutaneous area to help minimize the risk of catheter breakage.

The catheter assemblies 10, 10' can be removed without unnecessary cutting by using a scalpel or a cutting tool shaped to fit around the devices 14, 14'. Such a tool can be configured to have a hollow cylindrical cutting surface which has an inner diameter approximating the outer diameter $d_2$ of the fabric cuff 15. Upon insertion of the cutting tool around the device 14, the tool can be carefully forced over the device 14 such that the tissue around the cuff 15 is easily severed from the fabric. Once the tissue is severed, the catheter assembly 10, including the device 14 can be easily slid out of the subcutaneous area. The physician can then close the area quickly.

Preferably, as shown in FIGS. 5 and 5A, the catheter assembly 10 having a catheter stabilizing device 14 according to the present invention is removed from a subcutaneous location 40 without any surgical cutting. The assembly 10 may be removed by inserting a device 42 having a having a handle 44 and a head 46. The handle 44 has a distal end 48 which is attached to the head 46 for inserting into the lumen 18 of the catheter assembly 10 and a proximal end 50 which is held by the physician for inserting the device 42. Preferably the handle 44 extends in the longitudinal direction from the distal end 48 to the proximal end 50, and has a length sufficient to enable the head 46 to be positioned within the catheter stabilizing device 14, while the proximal end 50 of the handle extends outwardly from the proximal end 60 of the catheter assembly 10 a sufficient distance to enable the physician to manipulate the handle 44.

The head 46 and handle 44 may be formed as a single unit, or formed separately and fit together by soldering, snap-fit, mating threads or other similar attachment methods. The handle 44 and the head 46 may be made of any relatively rigid material, for example, steel or other metals, or a hard durometer plastic or elastomeric material. The head is preferably cylindrically-shaped if the internal surface of the catheter is generally circular in cross section, but the shape of the head 46 may be varied in order to conform to the internal surface 54 of the catheter assembly. While it is preferred that the shape of the head 46 conform to the shape of the internal surface 54 of the catheter assembly 10, it is not necessary as long as the head is shaped to fit within the lumen 18, and to sufficiently grip the surface 54, to dislodge the stabilizing device 14 from the surrounding tissue and pull the assembly from the subcutaneous location.

The head has an external gripping surface 52, which is preferably uneven, so that the head 46 can grip the internal surface 54 of the catheter assembly 10. The surface 52 may have raised projections such as small spikes, ribs and the like. Preferably, the surface 52 has threads 56 as shown in FIGS. 5 and 5A.

The diameter $d_3$ of the head 46, as measured in a direction perpendicular to the longitudinal axis of the device 42, when the head is generally circular in cross-section, is preferably larger than the diameter $d_4$ of the handle 44. The head 46 is sized such that upon insertion of the head 46 into the lumen 18 of the catheter assembly 10, the surface 52 grips the internal surface 54 of the assembly 10.

If threads 56 are provided, the head 46 may be rotated, by rotating the handle 44, such that the head is screwed into the lumen 18 for a snug fit between the gripping surface 52 and the internal surface 54 of the assembly 10. By gripping the internal surface 54, pulling force exerted on the proximal end 50 of the handle 44 will dislodge the cuff 15 of the stabilizing device 14 from the portion of the subcutaneous location 40 into which it has ingrown without surgical cutting. After dislodging, additional pulling force on the proximal end 50 of the handle 44 will remove the assembly 10 from the subcutaneous location 40.

For more easy insertion of the head 46 into the lumen 18, the head 46 preferably also has a tapered distal end 58 as shown in FIGS. 5 and 5A. The distal end 58 may be pointed or rounded, preferably, the distal end 58 of the head 46 is conical with a smoothly rounded tip.

The method for removing a catheter assembly having a catheter stabilizing device which includes a tissue ingrowth cuff, such as an assembly 10 as described above, ingrown into a subcutaneous location 40, preferably uses a device having a handle and a head having an external gripping surface, preferably the device 42 described above. The method includes inserting the head 46 into the proximal end 60 of the catheter in the lumen 18 by pushing the handle 44 of the device longitudinally into the lumen as shown in FIG. 5. The head is then further inserted into the lumen 18 by pushing the handle 44 until a distal end of the head 58 is substantially aligned with the distal end, i.e. the second side 34 of the first end piece 20 of the stabilizing device 14. The proximal end 50 of the handle 44 is then pulled outwardly in the longitudinal direction as shown in FIG. 5 to dislodge the tissue ingrowth cuff 15 from the subcutaneous location 40. Continued pulling will remove the assembly 10 from the location 40 without surgical cutting.

If threads 56 are provided to the surface 52 of the head 46 of the removal device 42, then, when the head 46 is being inserted, the proximal end 50 of the handle 46 should be rotated as shown in FIG. 5 such that the head is screwed into the lumen 18 for a more snug fit between the head 46 and the internal surface 54 of the catheter assembly 10.

This removal of the present assembly as described above is a significant improvement over prior art removal procedures in which the physician had to cut around the circumference and all edges of an ordinary fabric cuff such that the physician was, in effect, digging the cuff out of the tissue. Such a procedure causes increased bleeding and risk of infection. Further, due to the design of the end pieces 20, 22 of the device 14, the assembly slides out of the subcutaneous area much more easily minimizing the possibility of breakage or snapping of the catheter in the subcutaneous area. In addition, when the removal device 42 is used, no surgical cutting is required and the catheter assembly 10 is easily removed from the inside of the catheter with minimal risk of bleeding and infection to the patient.

The invention will now be described in accordance with the following non-limiting examples:

EXAMPLE I

Two tapered frustoconically-shaped end pieces formed of silicone and having 24 FR cylindrical openings extending through the end pieces are positioned on either side of a Dacron® cuff affixed by an adhesive layer to the external surface of a single-lumen catheter of a Tesio catheter assembly. The angle of taper of the frustoconically-shaped end pieces is 45°. The cuff is pre-cut to a rectangular shape 5 mm×25 mm in dimension and then affixed to the catheter such that the cuff fits around the catheter one time without overlapping. The end pieces are positioned such that the larger diameter sides abut the edges of the cuff. The end pieces are then subjected to heat by liquid vulcanization injection molding such that the internal surfaces of the end pieces are in full facing engagement and molded onto the external surface of the catheter.

EXAMPLE II

A mold is prepared having the shape of a 10 FR single lumen catheter of a Tesio catheter assembly having first and second end pieces positioned on a proximal portion of the catheter. The second side of the first end piece is 17 cm from the proximal end of the catheter and the second side of the second end piece is 22 mm from the distal end of the catheter. The end pieces are radially tapered at a constant rate of increasing radius from the external surface of the catheter toward first sides which lie in a plane perpendicular to the longitudinal axis of the catheter such that frustoconically shaped end pieces are formed and the angle of taper is 20°. The first sides have annular cross-sections and an outer diameter of 6 mm. The first sides are spaced longitudinally 3.5 mm from each other. The mold is filled with silicone and subjected to heat by injection molding to form a unitary catheter. The catheter is removed from the mold.

A Dacron® cuff as described in Example I and measuring 3.5 mm by 22 mm is affixed to the external surface of the catheter in the space between the frustoconically-shaped end pieces such that the edges of the cuff abut the first sides of the end pieces.

EXAMPLE III

A unitary base of a stabilizing device having two end pieces and measuring 1.7 cm longitudinally from the second side of the first end piece to the second side of the second end piece is formed by injection molding. The end pieces of the unitary base each have an angle of taper of 20°. The central portion of the base is 3.5 mm as measured longitudinally between the two end pieces and has a thickness measured from the interior surface of the central portion to the exterior surface of the central portion of about 0.5 mm. The unitary base has a 10 FR cylindrically-shaped opening extending through the base. The base is slid over a 10 FR single lumen catheter from a Tesio catheter assembly until the base is 17 cm from the proximal end and 22 cm from the distal end of the catheter. The unitary base is then heat molded to the exterior surface of the catheter by liquid vulcanization injection molding.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A catheter assembly, comprising:
   (a) a catheter having an external surface and at least one lumen extending therethrough; and
   (b) a catheter stabilizing device, comprising
      (i) a cuff having a first edge and a second edge, the cuff adhered to the external surface of the catheter;
      (ii) a first end piece having an external surface and an internal surface configured to conform to the external surface of the catheter in facing engagement and being permanently affixed to the external surface of the catheter, the external surface of the first end piece being tapered from a first side abutting the first edge of the cuff to a second side; and
      (iii) a second end piece having an external surface and an internal surface configured to conform to the external surface of the catheter in facing engagement and being permanently affixed to the external surface of the catheter, the external surface of the second end piece being tapered from a first side abutting the second edge of the cuff to a second side.

2. The catheter assembly according to claim 1, wherein the cuff is adhered to the external surface of the catheter by an adhesive.

3. The catheter assembly according to claim 1, wherein the first and second end pieces comprise a heat moldable material and are molded onto the external surface of the catheter.

* * * * *